(12) United States Patent
Giraud

(10) Patent No.: US 7,063,234 B2
(45) Date of Patent: Jun. 20, 2006

(54) METER STRIP DISPENSER ASSEMBLY

(75) Inventor: Jean-Pierre Giraud, Paris (FR)

(73) Assignee: CSP Technologies, Inc., Amsterdam, NY (US)

( * ) Notice: Subject to any disclaimer, the term of this patent is extended or adjusted under 35 U.S.C. 154(b) by 23 days.

(21) Appl. No.: 09/751,191

(22) Filed: Dec. 29, 2000

(65) Prior Publication Data

US 2002/0104849 A1 Aug. 8, 2002

(51) Int. Cl.
| | |
|---|---|
| B65G 11/16 | (2006.01) |
| B65G 59/00 | (2006.01) |
| B65H 3/00 | (2006.01) |
| B65H 1/08 | (2006.01) |
| G07F 11/16 | (2006.01) |

(52) U.S. Cl. .................. 221/271; 221/274; 221/232; 221/255; 221/235; 221/32

(58) Field of Classification Search ................ 221/235, 221/271, 274, 232, 255, 32
See application file for complete search history.

(56) References Cited

U.S. PATENT DOCUMENTS

| | | | | |
|---|---|---|---|---|
| 934,386 A | * | 9/1909 | Blekastad | 221/228 |
| 2,200,553 A | | 5/1940 | Illmer | |
| 2,265,696 A | * | 12/1941 | Mullins | 312/48 |
| 2,626,197 A | * | 1/1953 | Kollock | 312/55 |
| 2,889,076 A | * | 6/1959 | Van Schie | 221/232 |
| 2,994,464 A | * | 8/1961 | Krueger | 226/135 |
| 3,159,308 A | | 12/1964 | Passsavanti | |
| 3,446,343 A | | 5/1969 | Zimmer et al. | |
| 3,517,855 A | | 6/1970 | Hillis | |
| 3,728,081 A | | 4/1973 | Bidanset | |
| 3,917,090 A | | 11/1975 | Montagnino | |
| 4,045,102 A | * | 8/1977 | Austin | 312/61 |
| 4,088,276 A | | 5/1978 | Littleton | |
| 4,218,421 A | * | 8/1980 | Mack, Jr. et al. | 422/66 |
| 4,428,908 A | | 1/1984 | Ashley et al. | |
| 4,541,547 A | * | 9/1985 | Miknyocki et al. | 221/260 |
| 4,615,462 A | | 10/1986 | Sacherer et al. | |
| 4,690,303 A | * | 9/1987 | Draper et al. | 221/131 |
| 4,832,229 A | * | 5/1989 | Hackmann et al. | 221/25 |
| 4,883,197 A | * | 11/1989 | Sanchez et al. | 221/26 |
| 4,911,344 A | * | 3/1990 | Kahler | 221/232 |
| 5,056,682 A | | 10/1991 | Meyst et al. | |
| 5,119,969 A | | 6/1992 | Haber | |
| 5,244,116 A | * | 9/1993 | Keo | 221/232 |
| 5,271,522 A | * | 12/1993 | Ko et al. | 221/58 |
| 5,323,920 A | | 6/1994 | Harris et al. | |
| 5,353,956 A | * | 10/1994 | Wilson | 221/198 |
| 5,505,308 A | * | 4/1996 | Eikmeier et al. | 206/449 |
| 5,707,197 A | * | 1/1998 | Jager | 414/14 |
| 5,757,666 A | * | 5/1998 | Schreiber et al. | 364/509 |
| 5,788,064 A | * | 8/1998 | Sacherer et al. | 206/204 |
| 5,988,252 A | | 11/1999 | Carroll | |
| 6,036,924 A | * | 3/2000 | Simmons et al. | 422/100 |
| 6,102,250 A | | 8/2000 | Leo, Sr. | |
| 6,123,221 A | | 9/2000 | Simpson | |
| 6,176,119 B1 | * | 1/2001 | Kintzig | 73/53.01 |
| 6,302,855 B1 | | 10/2001 | Lav et al. | |
| 6,394,306 B1 | * | 5/2002 | Pawlo et al. | 221/2 |
| 6,406,922 B1 | | 6/2002 | Casterlin et al. | |
| 6,514,585 B1 | * | 2/2003 | Pearson et al. | 428/40.1 |
| 6,534,017 B1 | * | 3/2003 | Bottwein et al. | 422/104 |
| 6,682,704 B1 | * | 1/2004 | Bottwein et al. | 422/104 |
| 2002/0057993 A1 | | 5/2002 | Maisey et al. | |

* cited by examiner

Primary Examiner—Donald P. Walsh
Assistant Examiner—Michael E. Butler
(74) Attorney, Agent, or Firm—Greenberg Traurig, LLP

(57) ABSTRACT

The present invention is directed to diagnostic kits that house and deliver a carrier for an analyte, such as a test strip carrying an blood glucose analyte used by persons afflicted with diabetes in order to determine their blood glucose levels.

16 Claims, 8 Drawing Sheets

METER STRIP DISPENSER ASSEMBLY

FIELD OF THE INVENTION

The present invention is directed to diagnostic kits that house and deliver a carrier for an analyte, such as a test strip carrying a blood glucose analyte used by persons afflicted with diabetes in conjunction with determining their blood glucose levels.

BACKGROUND OF THE INVENTION

Numerous devices are known in the art for packaging and housing the test strips which contain any of a number of analytes used by persons in the medical arts, or persons who, due to a medical condition, must test for the presence, absence, or level of a substance in their body. For instance, persons with diabetes apply their blood to test strips, in order to determine their blood glucose levels.

SUMMARY OF THE INVENTION

The present invention is directed to a meter strip dispenser assembly which includes a housing containing components that when actuated, will dispense a test strip. Further the assembly includes a vial which contains a cassette that houses test strips, and further, an assembly that delivers the test strips to a location where they are displaced from the container.

The vial containing the cassette and test strips is situated within the housing. The housing is further provided with a button that is in engagement with a mechanism that moves a rod into contact with a test strip, and displaces it from the vial. In one embodiment, the test strip is movable from a first position within the vial to a second position partially outside the vial, and a third position in which it has been completely removed from the vial. In a further embodiment, the movement from the first to second to third position is dependent upon the actuation of the mechanism, which moves between positions to effect the aforenoted movements of the test strips.

In a further embodiment, a cassette is housed within the vial. The cassette is provided with a mechanism that moves test strips into a position from which they can be dispensed from the vial.

The vial used in the meter strip assembly is one that can be opened to permit access to the test strips housed within it. However, when the assembly is not in use, it may be desirable to seal the strips of from the environment to prevent strip degradation, something which could be brought about by humidity, among other things. Accordingly, the vial may be made resealable, such as by providing the vial with a cap or a lid that can be sealed onto the container body (or removed therefrom, as the case may be) as often as necessary. In yet a further embodiment, the vial is provided with a lip seal, in which the displacement of test strips can be pushes them through the seal and out of the container. In this arrangement, the vial remains in substantially sealed except in those brief moments when a strip is moved through the seal.

DETAILED DESCRIPTION OF THE PREFERRED EMBODIMENT

Meter Strip Dispenser

Figure 1:
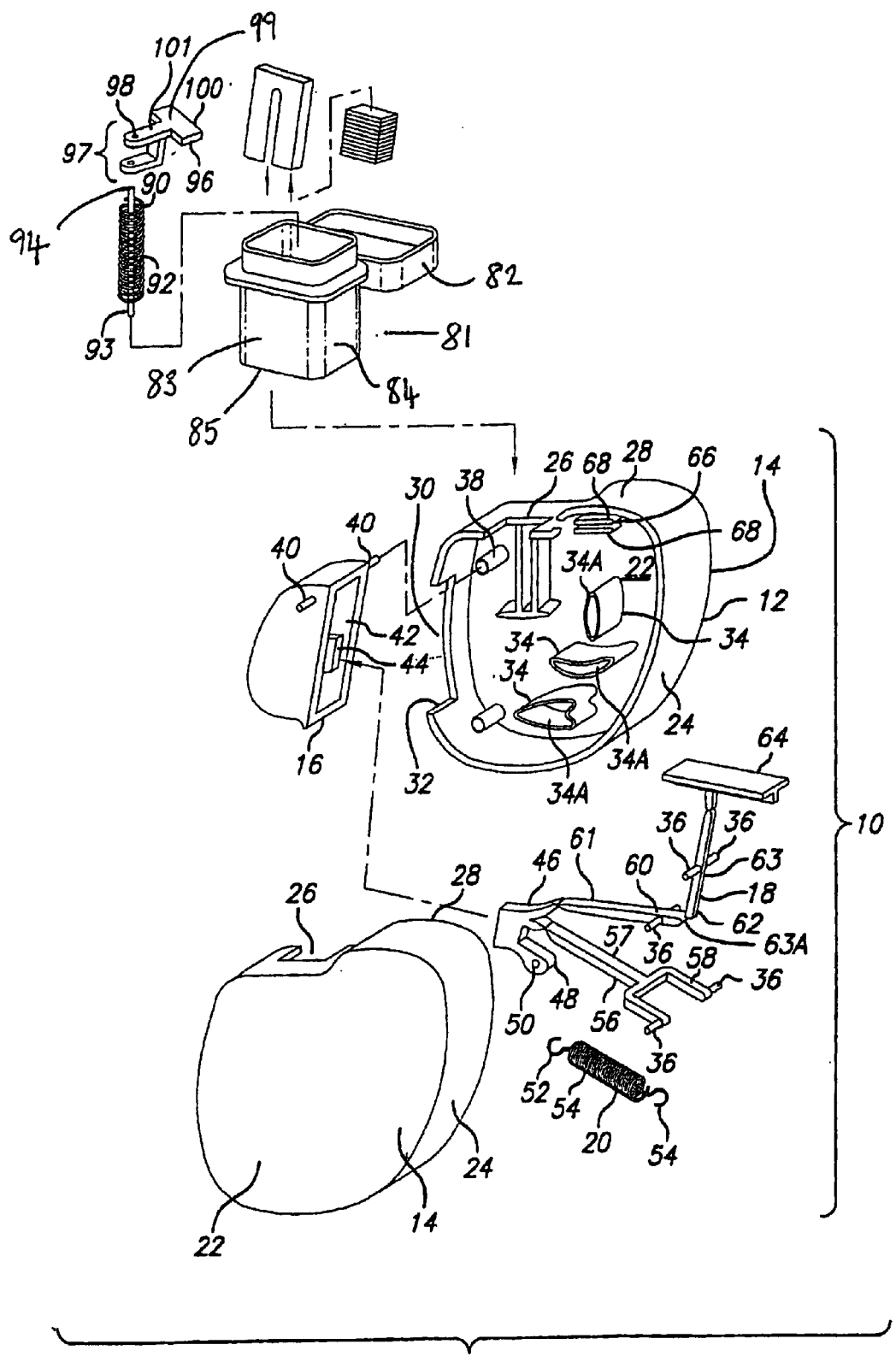
FIG. 1 is an exploded view of an embodiment of the assembly of the present invention.

The meter strip dispenser 10, shown in an exploded view in FIG. 1, is constructed of a housing 12 constructed of two halves 14, a button 16, an actuator 18, and a spring 20. Each of two halves are provided with opposing sides 22 and skirts 24 which extend perpendicular to the opposing sides 22. The skirts 24 are each provided at their edges with a profile complimentary to the profile of the other skirt, which permits the joinder of the halves, forming the predominant portion of the housing. The two halves can be joined together by screws, such as an arrangement in which a screw passes from one half and is received by apertures provided in the other half.

Each of the halves are provided with openings in their skirt regions 24, one opening 26 being provided on the top side 28, and the other opening 30 being provided on one of the long sides 32. When the halves are joined, the openings 26, 30 form an aperture in the top side 26 and an the aperture 30 in the long side 32. The vial containing the test strips resides in the top opening 26, while button 16 resides in the side opening 30.

Recesses 34A, defined by partitions 34, are provided on the inside of each half 14. The partitions 34 extend inwardly from the sidewalls, into the interior of the housing 12. The recesses receive pegs 36 that are provided on the actuator 18. When the halves 14 of the housing 12 are joined together, the pegs 36 reside within the recesses. The partitions 34 that define the recesses guide the actuator 18 along a path which results in the movement of a test strip out of the housing. Further, situating the pegs within the recesses stabilizes the actuator mechanism so that it is not able to engage in significant side-to-side movement within the housing. The actuator is, however, able to move along the path, as will be explained later.

Additional recesses 38 are provided up in the inside of each half 14. These recesses receive pegs 40 provided on the button 16. When the button is pressed, the button pivots inwardly around the pegs.

The inward facing side 42 of button 16 is provided with a recess 44 in which elbow 46 of the actuator 18 is snugly fitted, forming an interference fit. Elbow 46 is provided with knob 48 having aperture 50 which receives hook 52 of coil spring 54. A second hook 52 is provided at the other end of the spring, which is positioned around peg 56. The spring biases the button positioned to the inwards position.

Actuator 18 is provided with lower portion 56 which includes leg portion 57 which ramps upward to elbow 46. Lower portion 56 ends with fork 58, to which studs 36 are attached. Upper portion 60 of the actuator 18 includes leg 61 that ramps up and away from elbow 46 to bend 62. Vertical portion 63 extends from the bend 63 to pusher bar 64 which extends horizontally from upper position 63.

Pushing on the button 16 of the assembled housing moves the actuator, with the pusher bar moving in a substantially horizontal plane. The pusher bar is positioned within the slot 66 formed by the horizontally extending members located on the inside of the halves 14. Pusher bar 64 is slidably mounted within slot 66. Slot 66 guides the motion of the pusher bar 64.

All materials used in the making of the housing and associated components (with the exception of the spring, which preferably is a metal material) can be formed of plastic materials, according to well known extrusion, blow molding, or injection molding techniques.

Figure 2:
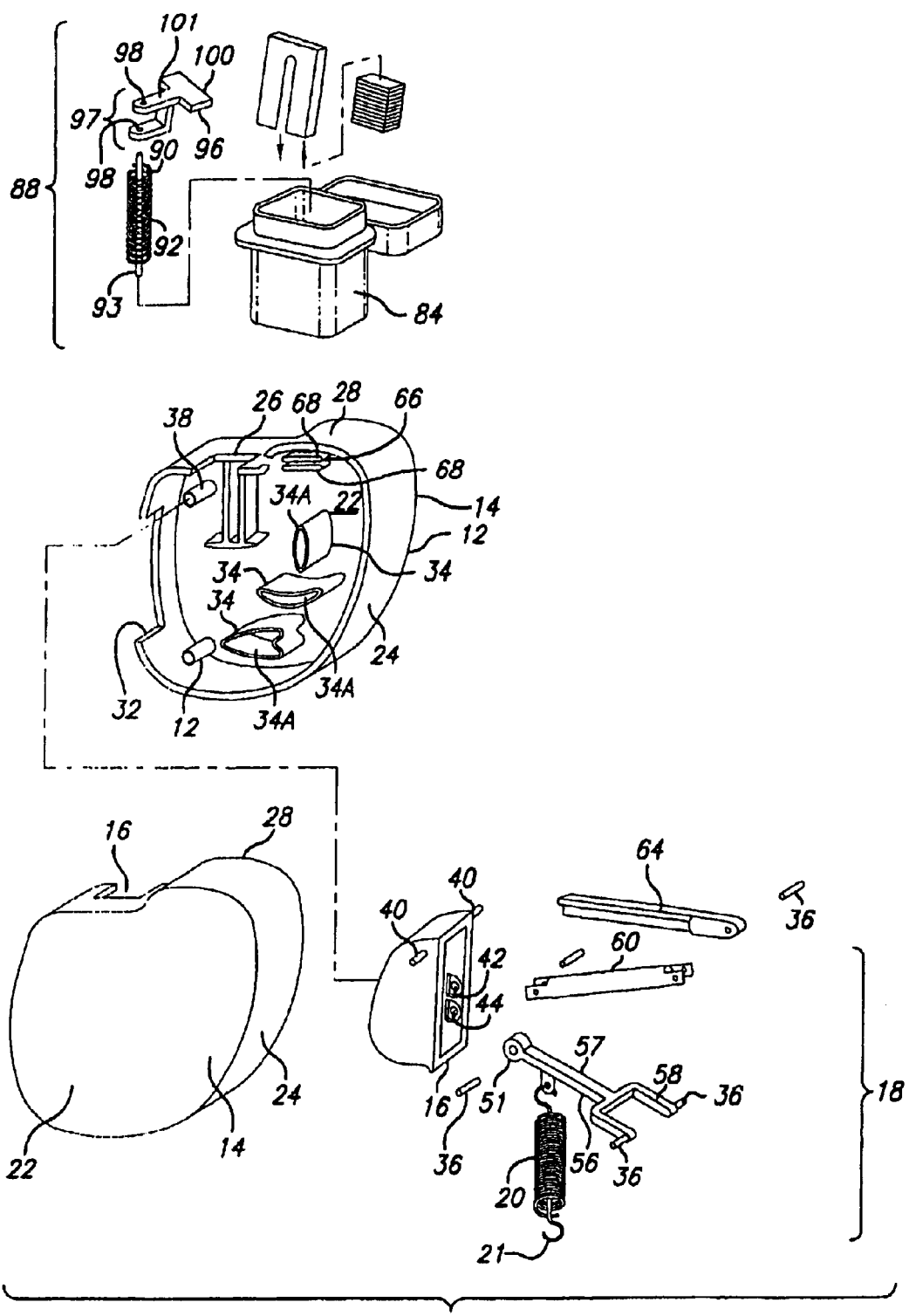
FIG. 2 is an exploded view of a further embodiment of the present invention.

In an alternative embodiment, shown in FIG. 2, the actuator 18 and pusher bar 64 are shown as discrete components, as opposed to a unitary construction as in the previous embodiment. Here, the actuator 18 is comprised of a distinct lower component 56, and upper component 60, and pusher bar 64. The lower component 56 is attached to the housing 10 by pegs 36 that are received in recesses within the housing. At one end, lower component 56 is joined to button at location 44 where peg is inserted into the aperture 51 on the end of the lower component 56. Lower component 56 is further provided with an aperture 50 that receives an end of spring 20. The spring 20 has another end 21 which is fixed to a peg or the like on the housing 12. The spring is biased to keep the button in an inward position.

The upper component 60 is joined to the pusher bar 64 by peg 36. Upper component 60 is joined to the button at location 44 where peg 36 is inserted into the aperture 51 on the end of the upper component 60. The pusher bar 64 resides within the slot 66. The pusher bar is positioned within the slot 66 formed by the horizontally extending members located on the inside of the halves 14. Pusher bar 64 is slidably mounted within slot 66. Slot 66 guides the motion of the pusher bar 64.

Vial and Cassette

Figure 3:
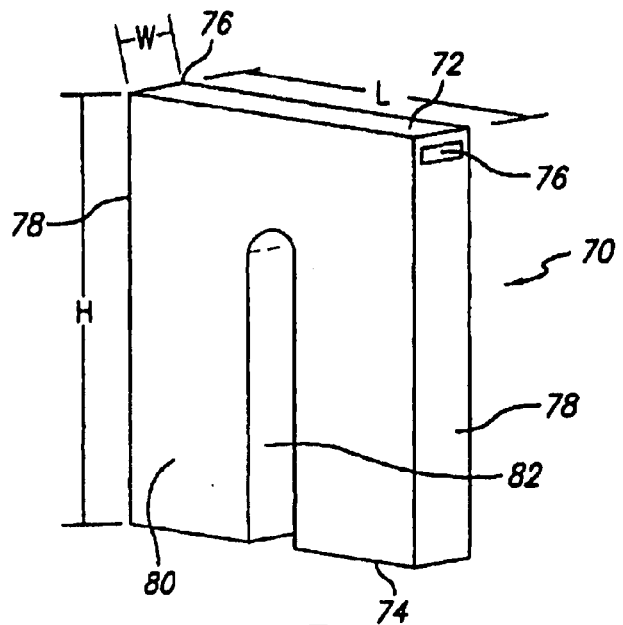
FIG. 3 is a perspective view of an aspect of an embodiment of the present invention.

Turning now to FIG. 3, the test strips are housed within a cassette 70 located within a vial 72. The cassette is a box-shaped apparatus that resides within the vial. The cassette is dimensioned and structured to receive a stack of test strips, dispense them one at a time, until the cassette has been emptied. The cassette is provided with length dimension L and width dimension W which accommodate the corresponding dimensions of the strip while maintaining the strips in an orderly stack. The cassette is further provided with a height dimension H that permits the cassette to hold a plurality of test strips. Merely for exemplary purposes, the height dimension H may be selected to allow for 50 test strips. However, the height dimension H may be varied to allow for a greater or lesser number of strips.

The cassette is closed on its top surface 72 and open on the bottom surface 74 (i.e., no bottom wall material is present at 74). The test strips are loaded into the cassette from the bottom 74. Apertures 76 are located near the top surface 72 of the cassette on the small sides 78 of the cassette. The apertures are large enough to permit the pusher bar 64 to move in and out of one of the slots, and to permit an individual test strip to be moved out of the other opening on the cassette.

At least one of the large sides 80 of the cassette is provided with a slot that runs in the height direction H. The slot runs from the bottom 74 of the cassette to the top 72 of the cassette, to at least the level of the opening 78.

The Vial and Cassette Construction

Vial 81 is of a conventional design having a cap 82, container 83, sidewall 84, and container bottom 85. The cap 82 is attached to the container by a hinge 86. Suitable vial constructions have been described in U.S. Pat. Nos. 5,911,937, 6,080,350, 6,124,006, and 6,130,263, as well as pending application Ser. Nos. 09/156,937, and 09/156,720. In another embodiment, a plug or other similar insert may be inserted into the container that is constructed of a desiccant plastic, or at least a portion of the interior of the container may be constructed of a desiccant plastic. The desiccant plastic is described in U.S. Pat. Nos. 5,911,937, 6,080,350, 6,124,006, and 6,130,263, as well as pending application Ser. Nos. 09/156,937, and 09/156,720 all of which are incorporated by reference herein.

The cassette 80 is loaded with strips, placed inside the vial, with lift apparatus 88 positioned under the test strips. The lift apparatus has a post 90 which is threaded through the coils of a helical spring 92. One end 93 of the spring 92 rests within the vial at the bottom thereof. At the top end 94 of the pole 92 a lift 96 is threaded over the pole 92. The lift 96 is provided with pole 92 engaging portion 97 in which apertures 98 are present in a solid surface 99. Pole engaging portion of lift is connected to the lift surface 100 by mid portion 101. The lift surface 101 is sized and shaped to fit within the cassette, and to move in the height dimension of the cassette without being unduly interfered with by the inside walls of the cassette.

In operation, the test strips are loaded into the cassette. The lift surface 100 is placed inside the cassette, so that the test strips rest on the lift surface 100. The midportion 101 is positioned within the slot 82 on the cassette. The biasing action of the spring, which presses against the floor of the vial container and the underside of the pole engaging portion 97, keeps the pole engaging portion elevated, so that the top most test strip of the stack is in position to be removed from the cassette.

Figure 3A:
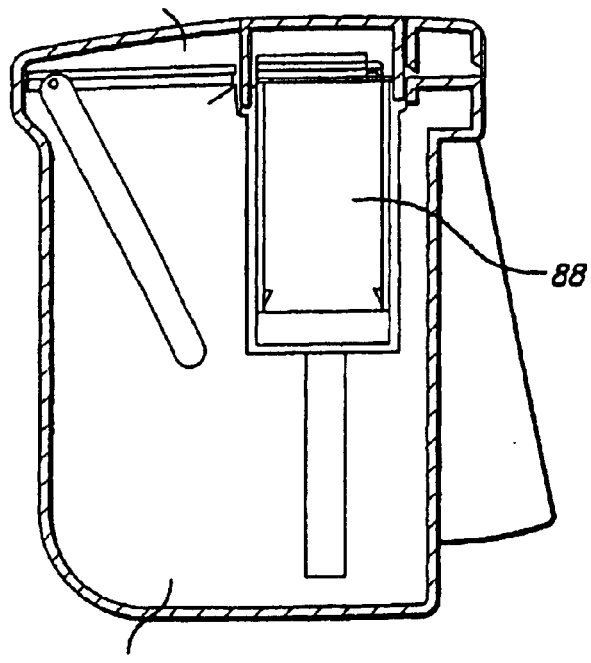
FIG. 3A is an elevational view of an embodiment of the present invention.

The vial and cassette, as loaded in the housing, is shown in FIG. 3A. To dispense a test strip, the user pushes the button 16 on the housing 10. This moves the actuator so that the pusher bar 64 enters through an opening 78 in the cassette, pushing the top strip of the stack partially out of the cassette and exposing it so the user can use it for testing, such as by wetting the strip with a bodily fluid, such as blood. After the strip has been wetted, a second push of the button, the pusher bar moves the test strip completely out of the canister. The upward biasing action of the spring on the lift move the lift upward when this test strip is dispensed, which moves the next highest test strip into the dispensing position.

Pushing button 16 inward activates components 60, 61 and 64. The pegs associated with these components which sit in the guide tracks keep the components in the tracks. In response to activation, the components move through the tracks and the pusher bar enters the vial.

Figure 4:
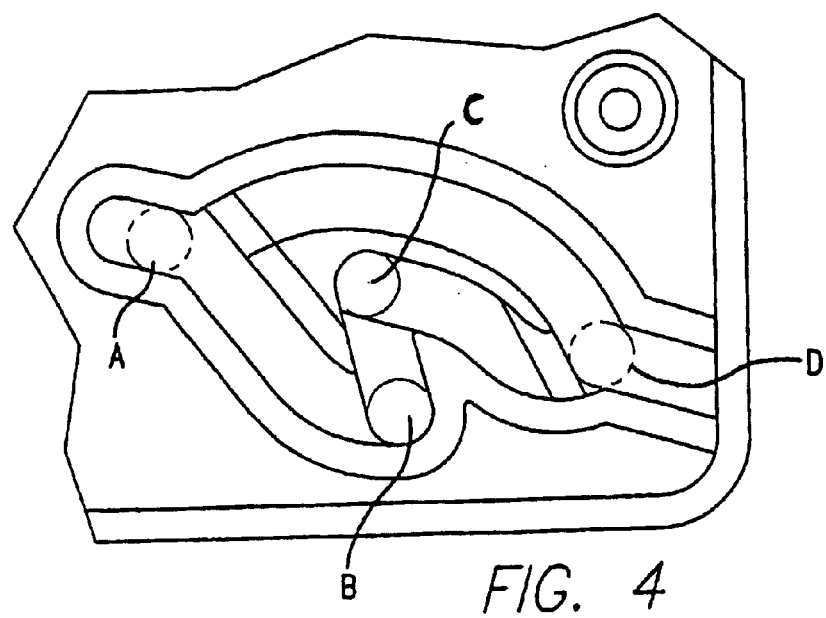
FIG. 4 is a side elevational view showing the movement of the pegs through the guide track.

FIG. 4 is a side elevational view which tracks the movement of a lower peg 36 through recess 36, which serves as a guide track. The peg starts at position A. When the button is pressed, the levers are activated. The peg tracks to position B, and continue on to position C, where it comes to rest. At position C, the pusher bar has pushed the test strip partially out of the opening in the cassette. When the button is activated a second time, the peg travels to position D, and then continues back to position A, where it comes to rest. At this position, the test strip has been pushed completely out of the cassette.

Figure 5:
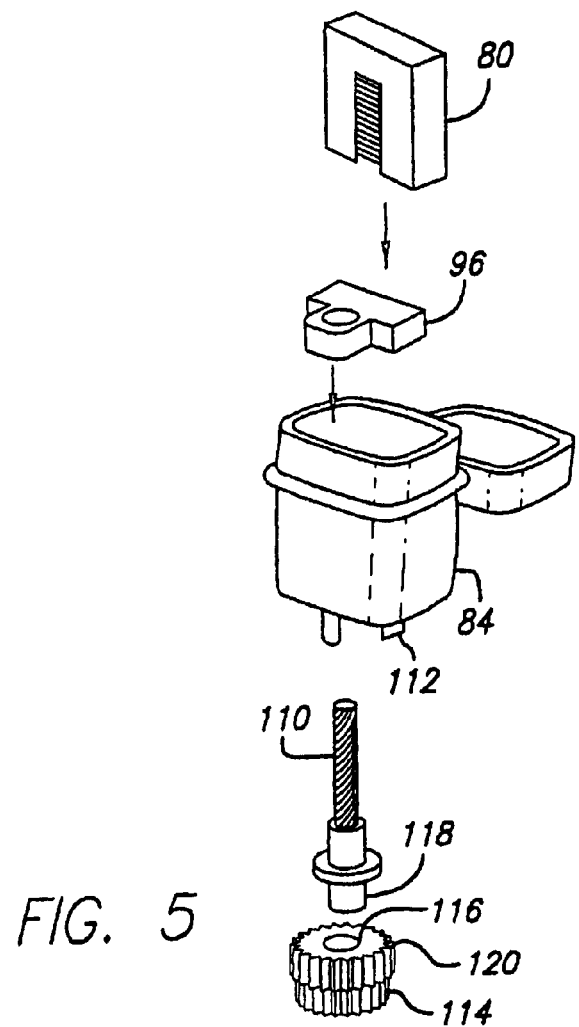
FIG. 5 is an exploded view of the vial, cassette, and lift mechanism of a further embodiment of the present invention.
Figure 6:
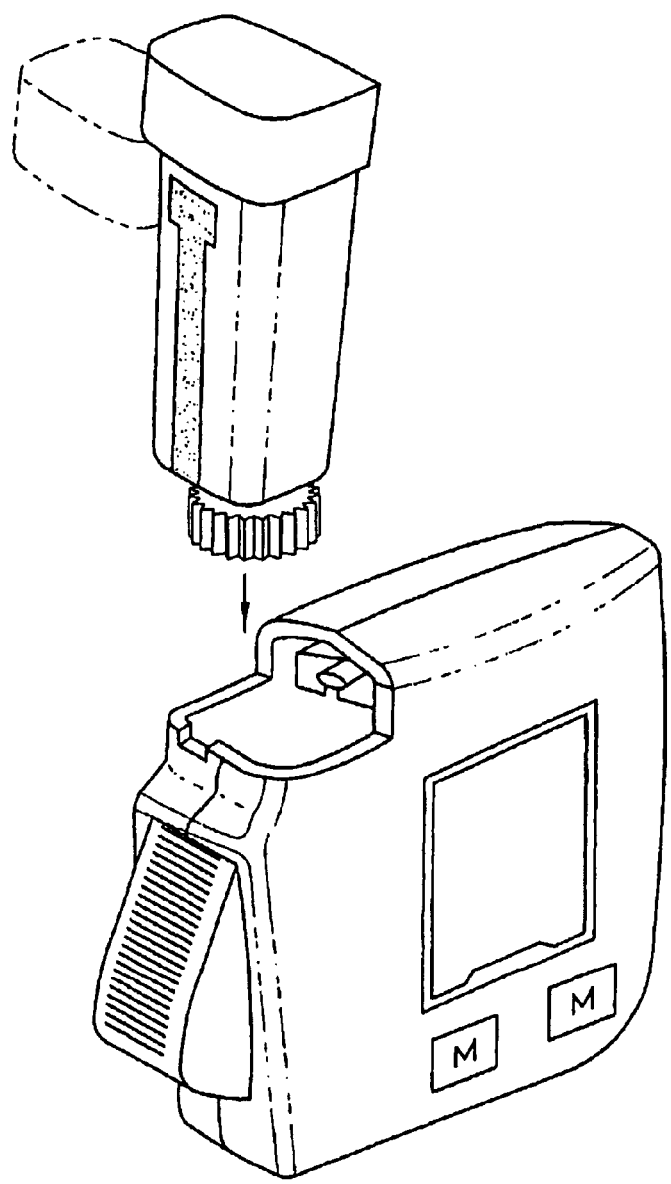
FIG. 6 is an exploded view of the assembly of the present invention showing the vial, cassette, and lift mechanism of FIG. 5.

In a further embodiment, shown in FIGS. 5 and 6, the lift apparatus has a different arrangement. The vial 84 is provided with an aperture (not shown) on its bottom surface, through which an activating rod 110 is inserted into the interior of the vial 84. The activating rod 110 is threaded, and receives the threaded aperture provided on the lift 96.

The bottom side of the vial is provided with downwardly extending sidewalls 112 which house a gear 114 having a threaded aperture 116 that receives the bottom threaded portion 118 of the activating rod 110. Spacer 120 is provided on the activating rod and rests on the gear.

Figure 6A:
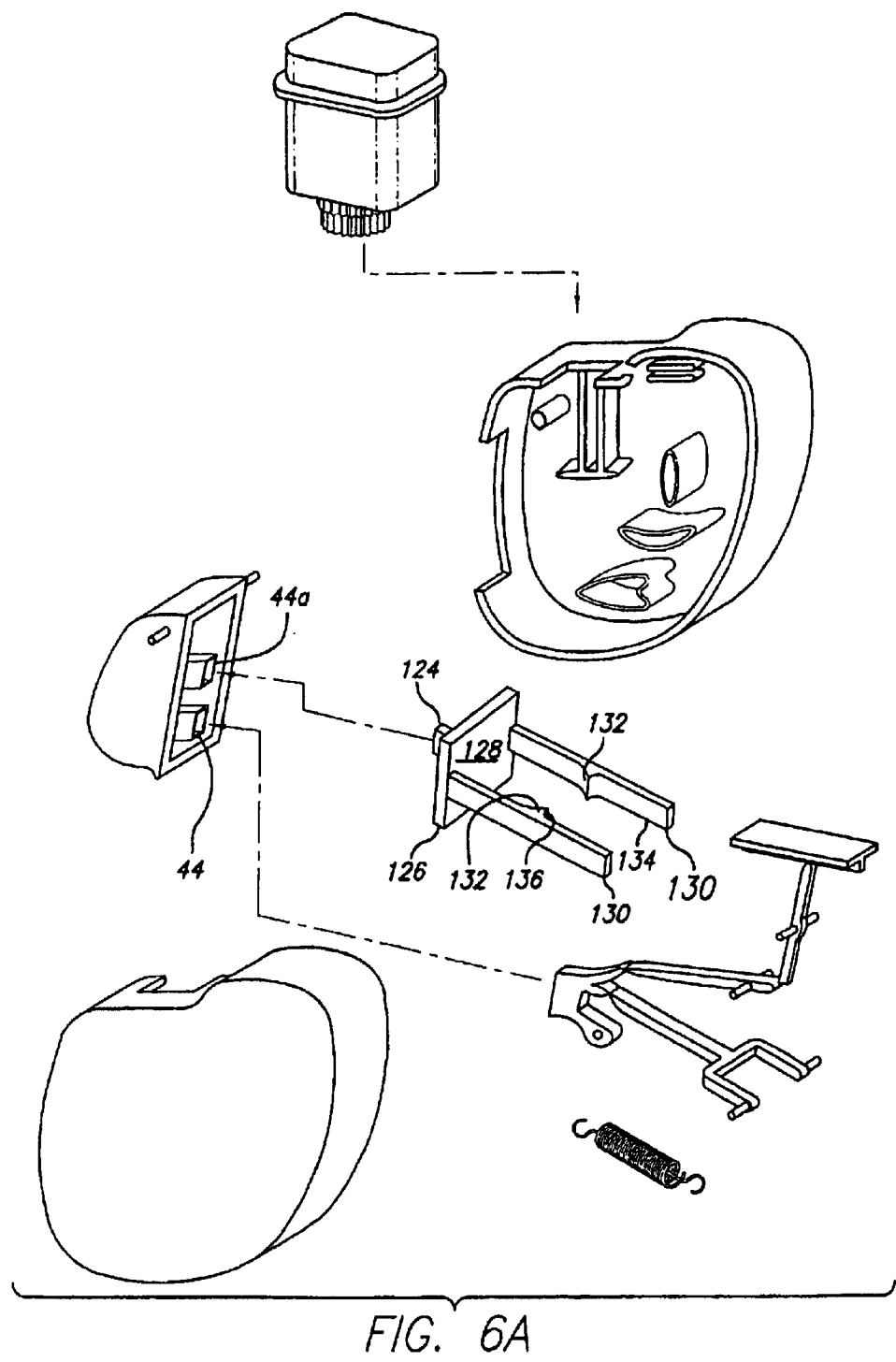
FIG. 6A is an exploded view of an embodiment of the assembly of the present invention

To accommodate this lift apparatus construction, the meter strip dispenser of FIG. 1 is modified to include a second recess 44a into which the butt end 124 of gear actuating member 126 is received. This arrangement is shown in FIG. 6A. Gear actuating member 126 has a base portion 128, on one side of which the butt end 124 extends. Two parallel rails 130 extend out from the opposite side of the base portion 128. Teeth 132 are provided on the inside walls 134 of the parallel rails 130. The teeth 132 may be angled out from the inside walls 134 and provided with a flat edge 136 facing away from the base portion 128.

When the button is pushed, the gear actuating member 126 moves forward, which causes the teeth 132 to engage the gear 120, and the activator rod 110 to rotate. However, the lift 96, which is threaded on to the activator rod 110, is constrained against rotation by the tight space in which it is located, i.e., the tight space immediately adjacent the vial sidewalls and the cassette. Accordingly, the activator rod 110 rotates through the lift, causing the lift to rise. Since the activation of the button turns the gear in an incremental movement, the lift rises in an increment, which corresponds to the thickness of a test strip. The test strip is dispensed in a manner consistent with the manner described with respect to the FIG. 1 embodiment.

Figure 7:
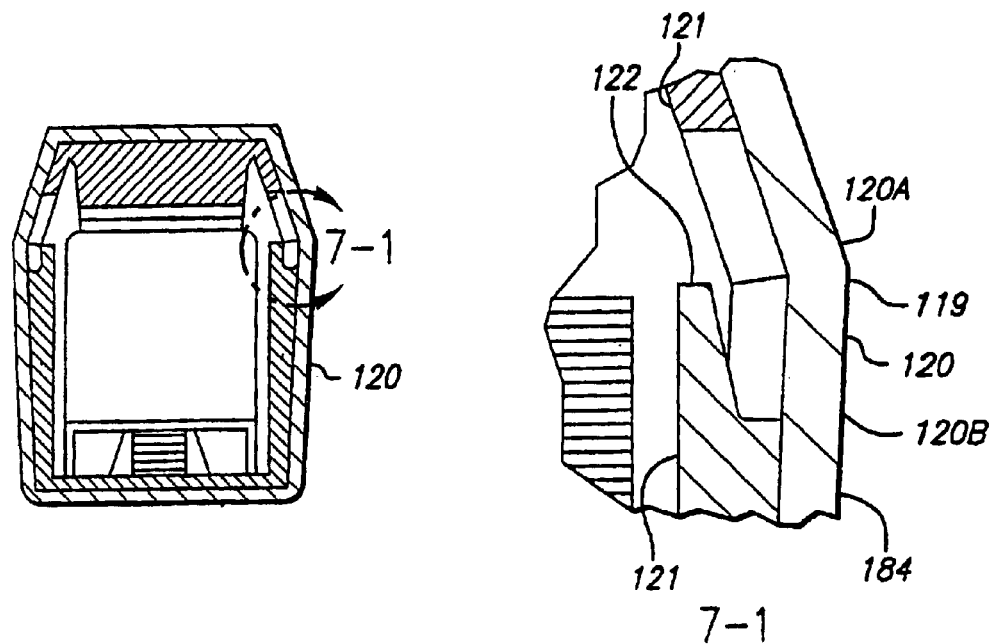
FIG. 7 is a side elevational view of a vial in a further embodiment of the present invention.
Figure 7A:
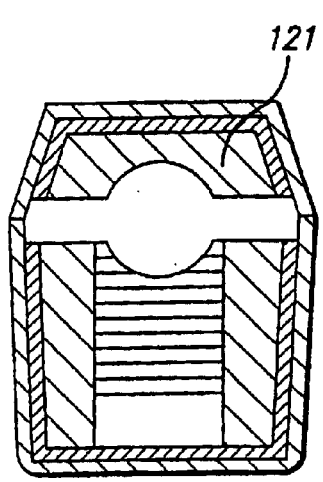
FIG. 7A is another view of the vial of FIG. 7.
Figure 7B:
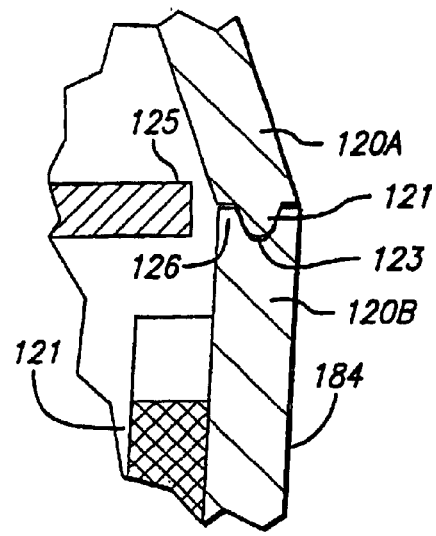
FIG. 7B is an alternative to the vial of FIGS. 7 and 7A.

Another suitable embodiment for a vial construction is shown in FIG. 7. In this embodiment, the vial is provided with a lip seal 119, through which the test strips pass when they are dispensed from the vial. At least a portion of the interior of the vial maybe lined with a desiccant plastic 121, which is discontinued in the region of the lip seal, providing a location for an opening through which the test strips are dispensed. See FIG. 7A. The lip seal 119 is located at the junction between the top side wall 120A and bottom side wall 120B. The outer container side walls 184 can be formed by blending a sufficient amount of elastomer with the carrier thermoplastic material. The flexibility of this material allows for the formation of the lip seal. That is, the lip seal exhibits a desirable degree of flexibility that permits the test strip to exit through the seal when subjected to the action of the pusher element. The desiccant plastic 121 may optionally be provided with tip 122 positioned so that the top test strip of the stack slides over it when it is dispensed from the container. FIG. 7B shows the absence of the tip.

The lip seal 119 can be modified in a yet a further embodiment in which a mating profile is provided in the thickness dimension of the elastomer has a mating profile that. That is, as shown in FIG. 7, the top side wall 120A is provided with an member 121 which extends beyond edge 125 of top side wall 120A. Member 121 mates with groove 123 provided in edge 126 of the bottom side wall 120B. This arrangement helps guide the lip seal components back together after a test strip has been dispensed through the lip seal.

In yet a further embodiment, the lift assembly may constructed of a coiling spring, such as a TENSATOR® spring. This spring tends to coil, so that as the spring coils from an initial elongated position, the stack of test strips placed on top is moved upward as the diameter of the coil increases incrementally. The spring is fixed at a first moveable end within the vial. In response to the dispensing of the test strips, the spring moves downward in the cassette, causing the spring to coil, moving the stack upward.

Figure 8:
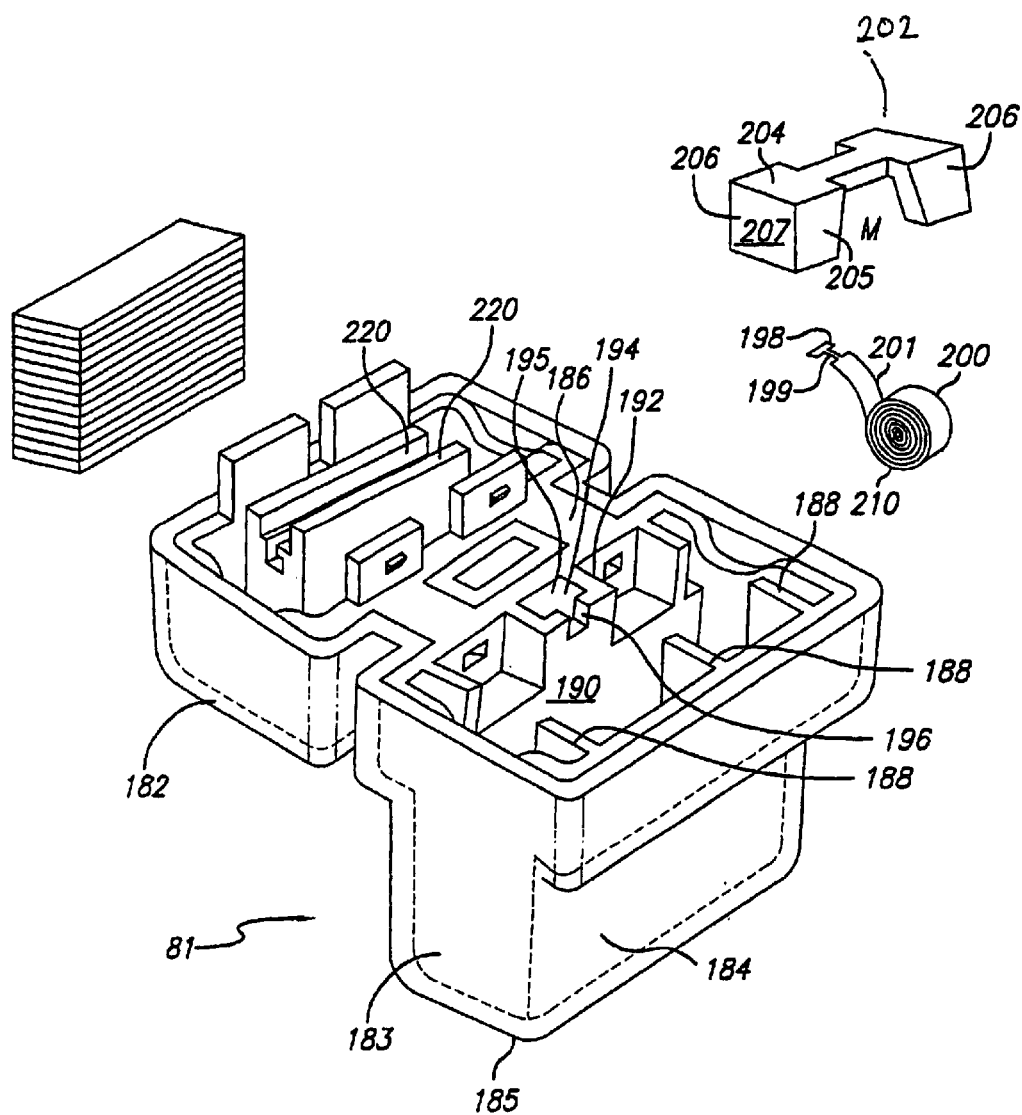
FIG. 8 shows a further embodiment of the present invention

FIG. 8 illustrates an embodiment of a vial construction in which the spring can be employed. The vial 81 is provided with the aforenoted components: the container 183, the cap 182, and the hinge 186. A number of ribs 188 extend from the container sidewalls 184 into the container interior, defining an open space 190 into which the test strips can be snugly fitted. (In this embodiment, housing the test strips in a cassette is optional.) The interior of the vial is further provided with an upper wall region 192 that define a basin 194 having a sink 195 and a notch 196. The upper portion of the spring 200 has a head 198 and neck portion 199 attached to the body 201 of the spring 200, which are respectively fitted in the sink 195 and the notch 196. The lift apparatus 202 is an element having a flat upper surface 204 upon which the test strips rest. Sidewalls 206 extend downward from the flat upper surface 204 on the long 205 and short sides 207 of the apparatus. On the long side 205 of the lift apparatus 202, the middle M of the apparatus is open. In other words, the downwardly extending long side 205 is discontinued in the middle M of the apparatus 202, providing a location where the coil 210 of the spring 200 can pass under the apparatus. With this arrangement, the apparatus rests on the coil 210, which increases in diameter as the stack of test strips is depleted.

When the head 198 and neck 199 of the spring 200 are placed within sink 195 and notch 196, the spring 200 is coiled, the coil 210 being near the top of the open space 190 in which the cassette or test strips is to be placed. When the test strips are placed on the coil 210, the spring 200 uncoils partially. The lid 182 of the vial 81 is shut. Preferably, the vial 81 is provided with a lip seal 119 such as that described in conjunction with FIG. 7. Test strips are dispensed from the vial by the movement of mechanisms previously described, with pusher bar 64 entering the vial from one end and pushing a test strip out through the other end. The underside of the vial lid is provided with guide tracks 220 that guide the pusher bar 64 along the path it takes when moving through the vial.

Numerous modifications and variations of the present invention are possible in light of the above teachings. It is evident that variations on the present invention may be constructed, which, in accordance with controlling law, are still subject to the claims written in view of the preceding disclosure.

I claim:

1. A meter strip dispensing assembly for dispensing a test strip, comprised of:

a housing;

a container for holding test strips, the container positioned within the housing;

a moveable body moveable between: (i) a first position that engages a test strip and displaces the test strip partially out of the housing through a container opening; and (ii) a second position that engages the test strip and displaces the test strip substantially entirely out of the housing through the container opening;

an actuator located on the housing, which actuator comprises a push button mechanism; and a moveable mechanism that connects the moveable body to the actuator;

wherein: (a) when the push button mechanism of the actuator is pushed, the moveable mechanism drives the moveable body to the first position; and (b) wherein the push button mechanism of the actuator is pushed again, the moveable mechanism drives the moveable body to the second position; and wherein the moveable body cycles back and forth upon repeated pushing of the push button mechanism of the actuator.

2. The meter strip dispensing assembly of claim 1, wherein the container is further comprised of:
a vial; and
a cassette positioned within the vial in which the test strips reside.

3. The meter strip dispensing assembly of claim 2, wherein the cassette has a top surface, is substantially open on a bottom surface, has sidewalls extending downward from the top surface, and has apertures provided on opposing sidewalls.

4. The meter strip dispensing assembly of claim 3, further comprised of a lift apparatus, the lift apparatus comprised of: a lift movably mounted over a vertically extending element having a top end and a bottom end, the bottom end resting on the vial bottom; and a biasing element situated over the vertically extending element, the lift resting against the biasing element which biases the lift towards the top end of the vertically extending element; wherein at least a portion of the lift is positioned within the cassette and is provided with a surface upon which test strips can rest.

5. The meter strip dispensing assembly of claim 4, wherein the cassette is provided with a vertically extending slot extending proximate from the bottom surface to proximate the top surface; wherein at least a part of the lift surface is situated within the cassette and the vertically extending element is positioned outside the cassette.

6. The meter strip dispensing assembly of claim 4, wherein the lift apparatus is situated entirely within the cassette.

7. The meter strip dispensing assembly of claim 1, wherein the movable mechanism is comprised of at least one lever engaged at a first end to the actuator and at a second end to the movable body.

8. The meter strip dispensing assembly of claim 4, wherein the movable mechanism is comprised of at least one lever engaged at a first end to the actuator and at a second end to the movable body, and the movable body is positioned to move in and out of one of the apertures in the cassette.

9. The meter strip dispensing assembly of claim 5, wherein the movable mechanism is comprised of at least one lever engaged at a first end to the actuator and at a second end to the movable body, and the movable body is positioned to move in and out of one of the apertures in the cassette.

10. The meter strip dispensing assembly of claim 3, further comprised of a lift apparatus, the lift apparatus comprised of: a lift provided with a threaded aperture mounted over a vertically extending threaded element having a top end and a bottom end, the vertically extending threaded element extending into an aperture in a bottom of the vial; means for rotating the vertically extending threaded element, wherein the lift moves upward in response to a rotation of the vertically extending threaded element, wherein at least a portion of the lift is positioned within the cassette and is provided with a surface upon which test strips can rest.

11. The meter strip dispensing assembly of claim 10, wherein the cassette is provided with a vertically extending slot extending from proximate the bottom surface to proximate the top surface; wherein at least a part of the lift surface is situated within the cassette and the vertically extending threaded element is positioned outside the cassette.

12. The meter strip dispensing assembly of claim 10, wherein the lift apparatus is situated entirely with the cassette.

13. The meter strip dispensing assembly of claim 3, wherein the cassette is enclosed within the vial, the vial being provided with a movable lip seal located in substantially the same plan as at least one aperture in the cassette, the lip seal being provided on a sidewall of the vial and is openable in response to a force applied from inside the vial when a test strip is moved against the seal.

14. The meter strip dispensing assembly of claim 13, wherein the lip seal is formed by blending an effective amount of elastomer with the carrier thermoplastic material used to construct the vial.

15. The meter strip dispensing assembly of claim 2, wherein the vial is further comprised of a desiccant plastic.

16. The meter strip dispensing assembly of claim 1, wherein the container is further comprised of a desiccant plastic.

* * * * *